United States Patent
Kumar

(10) Patent No.: US 6,800,753 B2
(45) Date of Patent: Oct. 5, 2004

(54) REGENERATED CELLULOSE AND OXIDIZED CELLULOSE MEMBRANES AS POTENTIAL BIODEGRADABLE PLATFORMS FOR DRUG DELIVERY AND TISSUE ENGINEERING

(75) Inventor: Vijay Kumar, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 10/234,276

(22) Filed: Sep. 4, 2002

(65) Prior Publication Data

US 2003/0064089 A1 Apr. 3, 2003

Related U.S. Application Data

(60) Provisional application No. 60/317,074, filed on Sep. 4, 2001.

(51) Int. Cl.[7] .................. C08B 16/00; A61K 31/717
(52) U.S. Cl. .................. 536/57; 536/56; 514/57; 424/42; 623/1.1
(58) Field of Search .............. 536/57, 56; 514/57; 424/424; 623/1.1

(56) References Cited

U.S. PATENT DOCUMENTS

| | | | |
|---|---|---|---|
| 3,666,750 A | * | 5/1972 | Griskin et al. |
| 4,289,723 A | * | 9/1981 | Leoni et al. |
| 4,543,410 A | * | 9/1985 | Cruz, Jr. |
| 5,134,229 A | * | 7/1992 | Saferstein et al. |
| 5,514,181 A | | 5/1996 | Light et al. |

FOREIGN PATENT DOCUMENTS

EP  0 636 377 A1 * 1/1995

OTHER PUBLICATIONS

Sinha et al. (Biomaterials, Medical Devices, and Artificial Organs (1985), 12 (3–4), 273–87) (abstract sent).*
Klemm et al.; Bacterial synthesized cellulose—artificial blood vessels for microsurgery; Prog. Polym. Sci. 26 (2001) 1561–1603; Progress in Polymer Science; Elsevier; Germany.

* cited by examiner

Primary Examiner—Samuel Barts
Assistant Examiner—Michael C. Henry
(74) Attorney, Agent, or Firm—McKee, Voorhees & Sease, P.L.C.

(57) ABSTRACT

The present invention describes the use of regenerated celluloses (RC) and (ORC) oxidized regenerated celluloses in the manufacture of scaffolds for drug delivery and tissue engineering. The RC and ORC are biodegradable and biocompatible. The carboxyl, aldehyde, or ketone groups present on the ORC scaffold serve as sites for cell, drug, protein and/or peptide attachment or further chemical modification to induce cell adhesion and subsequent proliferation. The method of manufacture of these membrane structures is simple, and produces flexible structures that maintain their strength when hydrated.

24 Claims, 4 Drawing Sheets

REGENERATED CELLULOSE AND OXIDIZED CELLULOSE MEMBRANES AS POTENTIAL BIODEGRADABLE PLATFORMS FOR DRUG DELIVERY AND TISSUE ENGINEERING

PRIORITY CLAIM

This application claims priority to provisional application Ser. No. 60/317,074 filed Sep. 4, 2001.

FIELD OF THE INVENTION

This invention relates to biodegradable tissue scaffolds and drug delivery systems comprising porous and non-porous, regenerated cellulose (RC) and oxidized regenerated cellulose (ORC) membranes, and methods of using the same.

BACKGROUND OF THE INVENTION

Organ or tissue failure is a major health crisis. Tissue engineering presents the potential to restore tissue function by using composites containing functional healthy cells from different sources (i.e. autogenic, allogeneic, or xenogeneic cells), and extracellular natural or synthetic polymers. Synthetic polymers must be biodegradable and biocompatible, be capable of fabrication into a porous three-dimensional membrane structure, and possess a range of physicochemical, mechanical, and degradative properties. The success of a promising polymer depends, in part, on the attachment and growth of the cells of interest on its surface. Thus, the surface chemistry, including hydrophobic/hydrophilic balance, mediates cellular response to the material and affects cell adhesion, proliferation, migration, and function on the surface.

A number of synthetic polymers, such as poly(glycolic acid), poly(lactic acid), poly(glycolide-co-lactide) copolymers, poly($\epsilon$-caprolactone), poly(dioxanone), and poly(glycolide-co-trimethylene carbonate) are currently being investigated as potential scaffolds for tissue engineering. Cellulose and its derivatives, such as cellulose acetates, have been extensively used as immobilizing matrices. However, these polymers are not biodegradable and, hence, are not suitable for use as implantable carrier systems.

Cellulose produced by microorganisms has been investigated for use as immobilizing matrices and implantable carriers. Microbial cellulose has a network structure in which very fine ribbon-shaped fibers composed of a highly crystalline and highly uniaxially oriented cellulose are complicatedly entangled with one another, and this network structure contains a large quantity of a liquid in interior voids thereof. Since the cellulose is composed of many ribbon-shaped fibers having a high crystallinity, the cellulose can resist external forces such as a tensile force even in the wet state. The microbial cellulose is not structurally different from a cellulose originating from a plant, but a high-order structure such as the above-mentioned structure is not found in the plant-originating cellulose although it is characteristic of the microbial cellulose. Accordingly, the microbial cellulose has a high strength though it is gelatinous.

Nevertheless, the use of microbial cellulose poses various problems compared with other widely used polymeric materials. More specifically, since thermoplastic polymeric materials represented by polyethylene and polyesters are made plastic by an application of heat or the addition of a softener, they can be molded into a desirable shape without changing their physical properties. Furthermore, these polymeric materials can be formed into any required shape or can be laminated by dissolution in a solvent or the like. In contrast, since microbial cellulose has the above-mentioned network structure without plasticity, if the microbial cellulose is dissolved in a solvent, the characteristics based on the characteristic high-order structure of the microbial cellulose are lost, and no substantial differences can be found between the microbial cellulose and the plant-originating cellulose. In addition, microbial celluloses must be treated to remove bacterial cultures prior to placement in the body.

Accordingly, it is a primary objective of the present invention to provide regenerated cellulose (RC) and oxidized regenerated cellulose (ORC) membranes as drug delivery systems and tissue scaffolds and methods of using the same.

It is a further objective of the present invention to provide RC and ORC membranes as drug delivery systems and tissue scaffolds that are biodegradable and biocompatible.

It is yet a further objective of the present invention to provide porous RC and ORC membranes as drug delivery systems and tissue scaffolds that have highly interconnected pore networks.

It is a further objective of the present invention to provide RC and ORC membranes as tissue scaffolds that are transparent and flexible.

It is still a further objective of the present invention to provide RC and ORC membranes as drug delivery systems and tissue scaffolds that provide attachment sites for drugs, proteins, and cells.

It is a further objective of the present invention to provide RC and ORC membranes as drug delivery systems and tissue scaffolds that are derived from a natural, non-microbial source.

It is a further objective of the present invention to provide RC and ORC membranes with good mechanical strength.

It is still a further objective of the present invention to provide RC and ORC membranes that may be modified to biodegrade at a particular rate.

The method and means of accomplishing each of the above objectives as well as others will become apparent from the detailed description of the invention which follows hereafter.

SUMMARY OF THE INVENTION

The present invention describes the preparation of regenerated celluloses (RC) and oxidized regenerated celluloses (ORC) as biodegradable drug delivery systems and tissue scaffolds. The RC and ORC composites are produced by first dissolving cellulose in a solvent system, then regenerating the cellulose into a desired scaffold structure. To produce porous scaffolds, a porogen is introduced in the solvent system to produce pores in the scaffold structure. The scaffold may then be oxidized to introduce carboxyl, aldehyde, and/or ketone functional groups on its surface. These functional groups serve as sites for cell attachment or further chemical modification to induce cell adhesion and subsequent proliferation.

The RC and ORC scaffolds produced in accordance with this invention are biodegradable and biocompatible, and therefore are suitable for implanting in the body. They may be used in a wide variety of biological and medical applications, including drug delivery, promotion of tissue and bone growth, as artificial blood vessels, as a substitute for human skin, dental implants, and micronerve surgery.

DETAILED DESCRIPTION OF THE DRAWINGS

DETAILED DESCRIPTION OF THE PREFERRED EMBODIMENT

Figure 1:
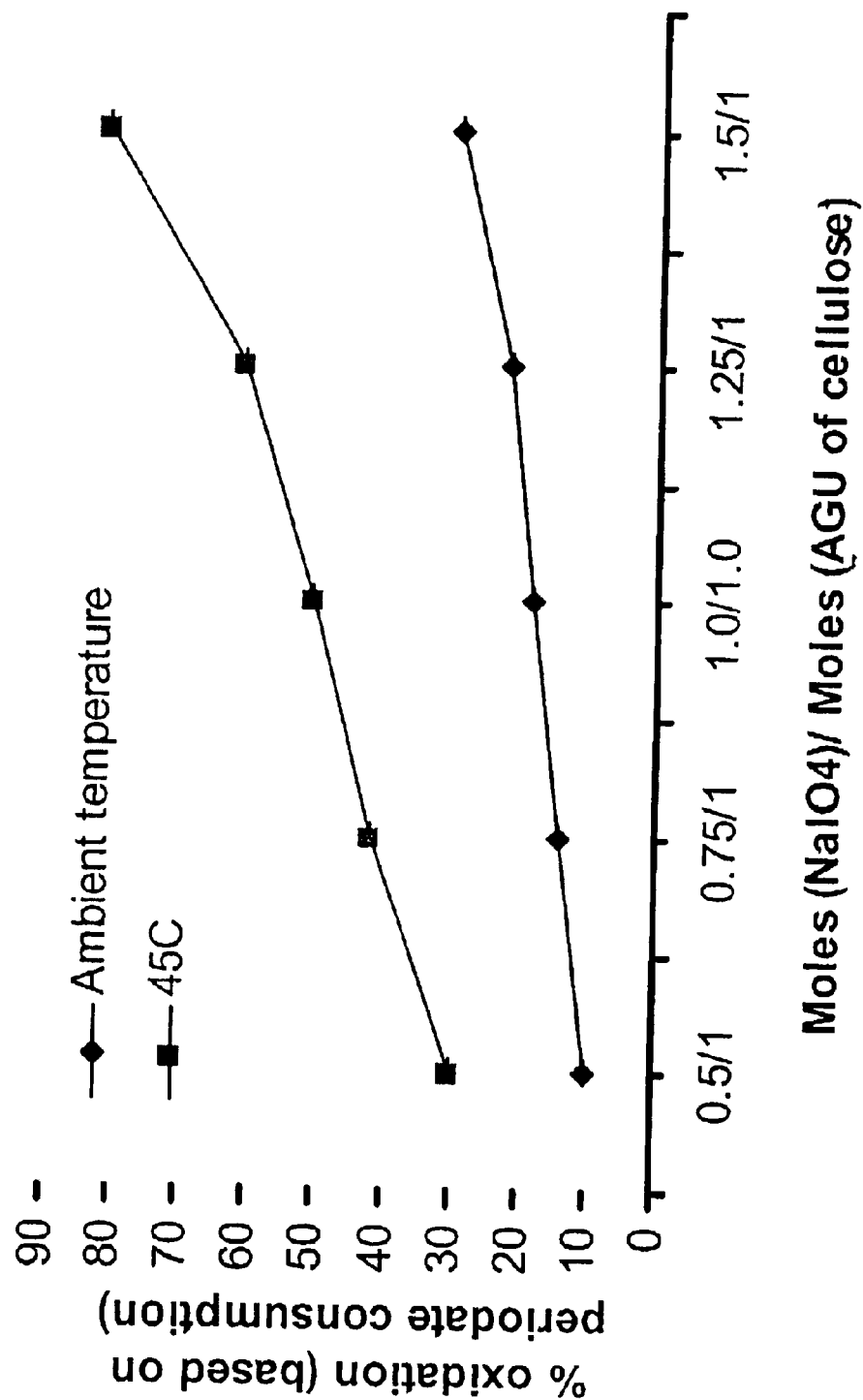
FIG. 1 is a graph comparing the percent oxidation of ORC at ambient temperature and 45° C., as described in Example 2.

The present invention relates to the development of cellulose compositions that function as biodegradable tissue scaffolds and as potential drug delivery platforms. The scaffolds are biocompatible, and the aldehyde, carboxyl, and/or ketone functional groups in the ORC provide favorable sites for the attachment of drugs, proteins, and peptides.

In general, the process of preparing the RC and ORC membranes of this invention involves dissolving cellulosic material in a solvent system. Examples of appropriate cellulosic starting materials include purified cotton, paper, cotton linters, α-cellulose, wood pulp, purified wood pulp, powdered cellulose, microcrystalline cellulose, and/or cellulose modified to other polymers. The preferred cellulosic starting material for use in this invention is cotton linter, powdered or ball-milled, with powdered being most preferred.

Microcrystalline celluloses are prepared by chemical disintegration of cellulose. Battista, O. A. (1950), Hydrolysis and Crystallation of Cellulose, Industrial and Engineering Chemisty 42:502–507; Battista U.S. Pat. No. 2,978,446. In general, the process of preparing microcrystalline cellulose involves hydrolyzing the cellulose with an aqueous dilute solution of a strong mineral acid, with occasional or constant stirring, at an appropriate temperature for a period until the level off degree of polymerization (level-off DP) cellulose composed of crystalline aggregates is achieved. Powdered celluloses, in contrast, are produced by mechanical disintegration of cellulose, wherein the cellulose source is first compacted into a dense sheet, then either milled to produce fine particles or converted into granules and then fractionated by passage through one or more sieves to produce the desired cellulose granules (see e.g. Morse, U.S. Pat. No. 4,269,859) or alternatively, a finally divided form of cellulose is dispersed in water and then treated with an agglutinating agent. Filtration, followed by washing the agglutinated solid first with water and then with a water-miscible organic solvent, and subsequently, lyophilizing and freeze-drying yields the product (see e.g. Morse, U.S. Pat. No. 4,438,263 (1984)).

Currently, both microcrystalline cellulose and powdered cellulose are commercially available under various trade names in different grades and types. Of these, the most common and widely used microcrystalline and powdered cellulose products are sold under the tradenames Avicel™ PH (FMC Corporation, Philadelphia, Pa.) and Solka Floc™ (Penwest Company, Patterson N.Y.).

A direct compression excipient called low crystallinity cellulose, having a degree of crystallinity value between 15 and 45% has been developed. See e.g. Banker and Wei, U.S. Pat. No. 5,417,984. It is produced by reacting cellulose with phosphoric acid first at room temperature for about an hour and then at 45–75° C. for about 2–10.5 hours, followed by precipitation in water.

Compared to microcrystalline cellulose (Avicel® PH-101), this material has been shown to possess superior properties as a binder.

The cellulose is dissolved in a solvent system which allows rapid regeneration of cellulose. Examples of appropriate solvents/solvent systems include, but are not limited to, ammonia/ammonium thiocyanate, calcium and sodium thiocyanate, zinc chloride, dimethylacetamide/lithium chloride, N-methyl-morpholine-N-oxide (N-MMO), aqueous solution of NaOH, aqueous NaOH/urea, NaOH/thiourea, and DMSO/paraformaldehyde. Persons skilled in the art can readily ascertain other appropriate solvents for this purpose.

A combination of DMSO (dimethyl sulfoxide) and paraformaldehyde is preferred for dissolving the cellulosic source. The paraformaldehyde reacts with the hydroxyl groups in the cellulosic source to produce methylolcellulose. The cellulose is then rapidly regenerated when exposed to water.

The reaction mixture is heated to about 80–125° C., with optional agitation, for a period of time effective to dissolve or suspend the cellulose, e.g. about 0.5–8 hours, and preferably about 2–6 hours.

With respect to the preferred DMSO/paraformaldehyde system, the cellulose may be added to the system all at once. However, the preferred method is to first add the cellulose to the DMSO, allowing it to swell for 30 minutes to one hour, then adding the paraformaldehyde to the reaction mixture in portions or all at once.

The cellulose is recovered by placing the cellulose solution in water. Preferably, the cellulose solution is spread or cast on a petri dish, glass plate, hollow tube, or other desired molding apparatus, and then allowed to regenerate in water. Optionally, the cast solution may be exposed to air for 24 hours or placed in a high humidity chamber, which provides more gradual hydration of the product, and ultimately results in a more homogenous regenerated scaffold.

Once recovered from the reaction mixture, the regenerated cellulose is optionally treated with an oxidizing agent to produce oxidized regenerated cellulose containing carboxyl, aldehyde, and/or ketone functionalities. These functional groups provide attachment points for drugs, proteins, peptides, cells, and other biological materials, such as growth factors, morphogenetic proteins (BNP), etc. Examples of appropriate oxidants include, but are not limited to, gaseous chlorine, hydrogen peroxide, peracetic acid, chlorine dioxide, nitrogen dioxide (dinitrogen tetraoxide), persulfates, hypochlorous acid, hypohalites or periodates. Preferred oxidizing agents include nitrogen oxide and alkaline metal periodates, with sodium or potassium periodate being most preferred.

The type of oxidant used will determine the type of functional groups on the scaffold. For example, using a periodate as the oxidant will yield only aldehyde functional groups. In comparison, using a nitrogen oxide as an oxidant will only yield carboxyl groups. Further, the use of hypochlorite as an oxidant will yield a combination of aldehyde, carboxyl, and ketone groups.

The concentration of the oxidant(s) in the solution depends on the extent of oxidation desired. Ratios of 0.5:1 to 1.5:1 of oxidant to repeating anhydroglucose (AGU) unit of regenerated cellulose is preferred. Generally, the higher the concentration of oxidant used, or the longer the reaction period, the higher the degree of oxidation. In turn, the more highly oxidized the cellulose, the faster the degradation of the scaffold when placed in the body. Therefore, biological scaffolds having particular degrees of degradability may be produced depending on the application and use of the scaffold.

The oxidation reaction is carried out for a period of time sufficient to achieve the desired oxidation level. Again, the longer the reaction is allowed to continue, the greater the degree of oxidation.

The oxidation reaction may be conducted at ambient temperature, or at an elevated temperature of up to about 75° C., depending on the nature of the oxidant being used. The inventor has determined that the degree of oxidation is higher at temperatures higher than room temperature.

To prepare the ORC-polymer composite, an oxidized scaffold having carboxyl or aldehyde functional groups may be dipped or coated in a solution that includes a polymer having an amine group, such as chitosan, and allowing the scaffold to dry.

In addition, dipping or placing an oxidized scaffold with aldehyde functional groups in a solution having polymer with amine groups and subsequently heating at a temperature of 40–80° C. produces an amine-bonded oxidized cellulose-polymer scaffold.

Optionally, the cellulose may be treated to create pores in its surface. The addition of pores increase the surface area of the scaffolds of this invention. Pores also allow for better attachment and proliferation of living cells and tissue. Non-porous scaffolds are less suitable for this purpose, and are generally more appropriate for use as a drug delivery vehicle, for example.

To create pores in the scaffold, a porogen is placed in the solvent system used to dissolve the cellulose prior to casting. The porogen may comprise any material that is insoluble in DMSO, or the solvent(s) used to initially dissolve the cellulosic source. Examples of suitable porogens include carbohydrates such as sucrose, lactose, galactose, and fructose, as well as ionic salts, such as sodium chloride, potassium chloride. The preferred porogen is sodium chloride.

With increasing particle size of the porogen, an increase in pore size is observed. Further, as particle size range increases, there is an increase in irregularity of pore sizes and shapes. Pore shapes are mostly circular and elliptical. For the largest size range, the pore size on the surface varies from very small to very large interconnecting pores. For optimum cell growth, the pores preferably have an average surface pore diameter of from about 80–90 $\mu$m, which therefore requires a porogen having the same particle size range. Persons skilled in the art may readily appreciate, however, that a different pore size may be desired depending on the ultimate use of the scaffold, and/or the types of biological materials to be anchored to the scaffold.

Porosity increases significantly with increasing amount of porogen. Further, the amount of porogen directly affects the configuration of the pores, i.e. the higher the concentration of porogen, the more highly interconnected the pore network. The presence of interconnected pores is an important feature for a scaffold to have, because it facilitates the organization and consequent proliferation of cells. It is preferred to have a scaffold having a more highly interconnected pore network.

Following addition of the porogen, the cellulose is regenerated in water by spreading the product on a plate or other physical structure as already described above. The product is then preferably immersed in a water bath, high humidity chamber, or subjected to other cellulose regenerating system. The resulting product is a porous, regenerated (RC) or oxidized, porous, regenerated cellulose membrane (ORC) that may be used as a scaffold for attaching various drugs, proteins, peptides, cells, and other biological materials. Persons skilled in the art can readily ascertain other appropriate methods of creating pores in the scaffolds of this invention.

The RC and ORC produced in accordance with this invention is characterized as being composed of cellulose having low crystallinity, having a high surface orienting property and a high strength, gradually biodegradable in a human or animal, and exhibiting a very good biocompatibility.

The RC and ORC of the present invention offer a wide range of special applications in human and veterinary medicine, and may be used for any and all indications of previously described scaffolds, and for other purposes not yet literally disclosed in the art, but readily ascertainable by persons skilled in the art. For instance, the high mechanical strength in the wet state, substantial permeability for liquids and gases, and low irritation of skin make the scaffold of this invention useful as an artificial skin for temporary coverage of wounds. The scaffold also has wide applications in tissue repair, surgery, and dental implants. For example, the scaffold may be used to recover periodontal tissues.

Through the use of gas permeable molds, cellulosic products of virtually any shape may be produced. The moldability of the cellulosic materials of this invention, as well as its inner surface quality, consistency, microdimensions ($\leq$6 mm in diameter), and mechanical strength make it appropriate as substitution material for blood vessels (following attachment of the endothelial cells in the lumen of the hollow tube in vitro), as described in different patents and publications. See e.g. EP Patent 0 186 495, JP Patent No. 08126697, JP Patent No. 03272772, D. Klemm et al. Prog. Polm. Sci. 26 (2001) 1561–1603, the disclosures of which are hereby incorporated by reference. The scaffolds of this invention may also be used as protective covers for micronerve sutures, an artificial skin, a cultured skin carrier, and a carrier for the mass culture of cells and an additive to the interior of the oral cavity.

In addition to the above-mentioned composite, scaffolds comprising the RC or ORC and an auxiliary material may be prepared. Appropriate biodegradeable auxiliary materials for this purpose include water-soluble, polar solvent-soluble or hydrophilic gel-forming polymeric materials such as agar, dextran, polyacrylamide, polyvinyl pyrrolidone, alginic acid salts, hyaluronic acid, curdlan, polyacrylic acid salts, heparin, sulfated polysaccharides, pullulan, carrageenan, glucomannan, cellulose derivatives, polyethylene glycol, polyvinyl alcohol, gelatin, collagen, laminitol, fibronectin, keratin, silk hydrolyzate, polyamino acids, poly-organic acids and enzymes. The RC/ORC scaffold is combined with an auxiliary material as mentioned above by means such as impregnation, lamination or adsorption to obtain a composite. Furthermore, a composite comprising a gelatinous auxiliary material included in the three-dimensional structure of the RC/ORC, and a composite comprising a fibrous auxiliary material entangled with the texture of the cellulose can be obtained.

As another example, the RC/ORC of the present invention may be used as a carrier for culturing animal cells inclusive of human epidermal cells, whereby animal cells can be cultured at a high density and a high propagation speed. Furthermore, the RC/ORC can be used as a carrier for culturing animal cells.

It may be possible to manufacture a product obtained by culturing human epidermal cells substantially in the monolayer state on the sheet-shaped scaffold of the present invention as a vulnerary cover or artificial skin to be applied to the affected skin such as the burnt or wounded skin. This product can be obtained in a relatively short time, and it is sufficient if the sheet-shaped RC/ORC product is applied to the affected part so that the epidermal cell layer adheres to the affected part. When the cellulose on the top surface is dried, an air-permeable and cell-impermeable porous protecting layer is formed. In the case where such an artificial skin is prepared and applied according to the conventional technique, a method must be adopted in which epidermal cells are cultured in multiple layers on a carrier over a long period (Howard Green and Olaniyi Kehinde, Proc, Natl, Acad, Sci, USA 1979, 76, 5665–8), the cultured cell layer is peeled from the carrier, the cell layer is applied to the skin so that peeled surface (the active side) of the cell layer adheres to the affected part, and the applied cell layer is covered with a protecting material such as a gauze pad.

The following examples are offered to illustrate but not limit the invention. Thus, they are presented with the understanding that various modifications may be made and still be within the spirit of the invention.

EXAMPLE 1

Preparation of ORC Membranes with Different Oxidation Levels and Porosities Purpose Oxidized cellulose containing aldehyde groups is a biocompatible and biodegradable polymer. The purpose of this study was to develop and characterize ORC membranes as potential drug delivery platforms.

Methods

Porous ORC membranes with different oxidation levels were prepared from regenerated cellulose membranes, produced from a mixture of methylolcellulose and sodium chloride in DMSO by solution casting and regenerating in water, by treatment with an aqueous solution of sodium metaperiodate ($NaIO_4$) for an hour at room temperature and at 45° C. The percent oxidation levels of ORC membranes were determined using periodate consumption and carbonyl content determination methods. The membranes were characterized by scanning electron microscopy (SEM), X-ray diffractometry (XRD) and infrared spectroscopy (IR).

Results

The oxidation of the regenerated cellulose membranes increased linearly with increasing concentration of $NaIO_4$. The percent carbonyl content of ORC membranes varied from about 12% to 63% at room temperature and from about 21% to 80% at 45° C. The XRD results indicated both regenerated cellulose and ORC embranes to contain the cellulose II-type lattice. The IR spectra of ORC membranes showed a characterisitc carbonyl peak at 1736 cm$^{-1}$ due to aldehyde groups. The SEM images revealed ORC membranes to be porous. The degree of porosity and pore size varied depending on the size and amounts of salt particles used to cast the films.

Conclusion

Results demonstrate that ORC membranes with different oxidation levels and porosities can be prepared by varying the concentration of $NaIO_4$, temperature, and quantity of salt particles. The aldehyde groups present on the membranes offer potentially favorable sites for the attachment of drugs, proteins, and peptides.

EXAMPLE 2

Preparation of Porous Regenerated Cellulose Membrane Using Salt Leaching Technique Below is a flow chart showing a preferred manufacturing method of the non-porous (A) and porous (B) RC and ORC of the present invention:

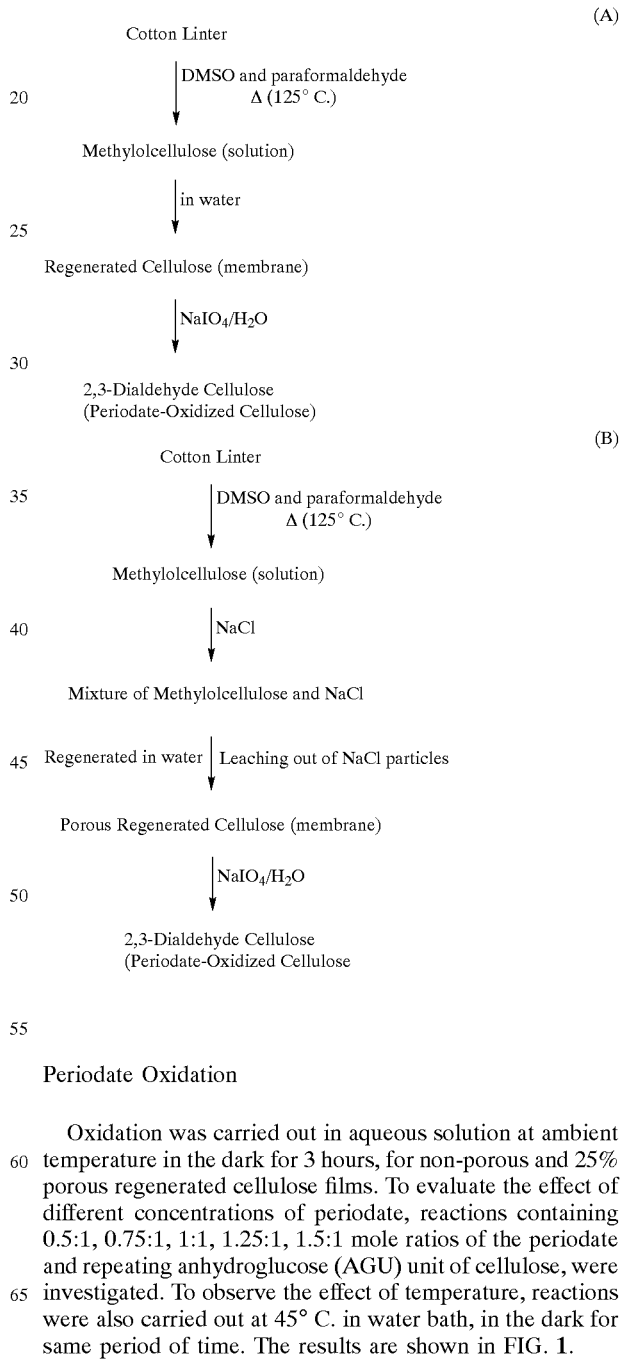

Periodate Oxidation

Oxidation was carried out in aqueous solution at ambient temperature in the dark for 3 hours, for non-porous and 25% porous regenerated cellulose films. To evaluate the effect of different concentrations of periodate, reactions containing 0.5:1, 0.75:1, 1:1, 1.25:1, 1.5:1 mole ratios of the periodate and repeating anhydroglucose (AGU) unit of cellulose, were investigated. To observe the effect of temperature, reactions were also carried out at 45° C. in water bath, in the dark for same period of time. The results are shown in FIG. 1.

Determination of Percent Oxidation

Periodate consumption was determined by measuring the absorbance at 290 nm$^2$:

$$\% \text{ oxidation} = \frac{[\text{Periodate consumed}(g) * \text{MW}(\text{NaIO}_4) / \text{MW}(AGU)]}{\text{Weight of cellulose membrane}(g)} * 100$$

Figure 2:
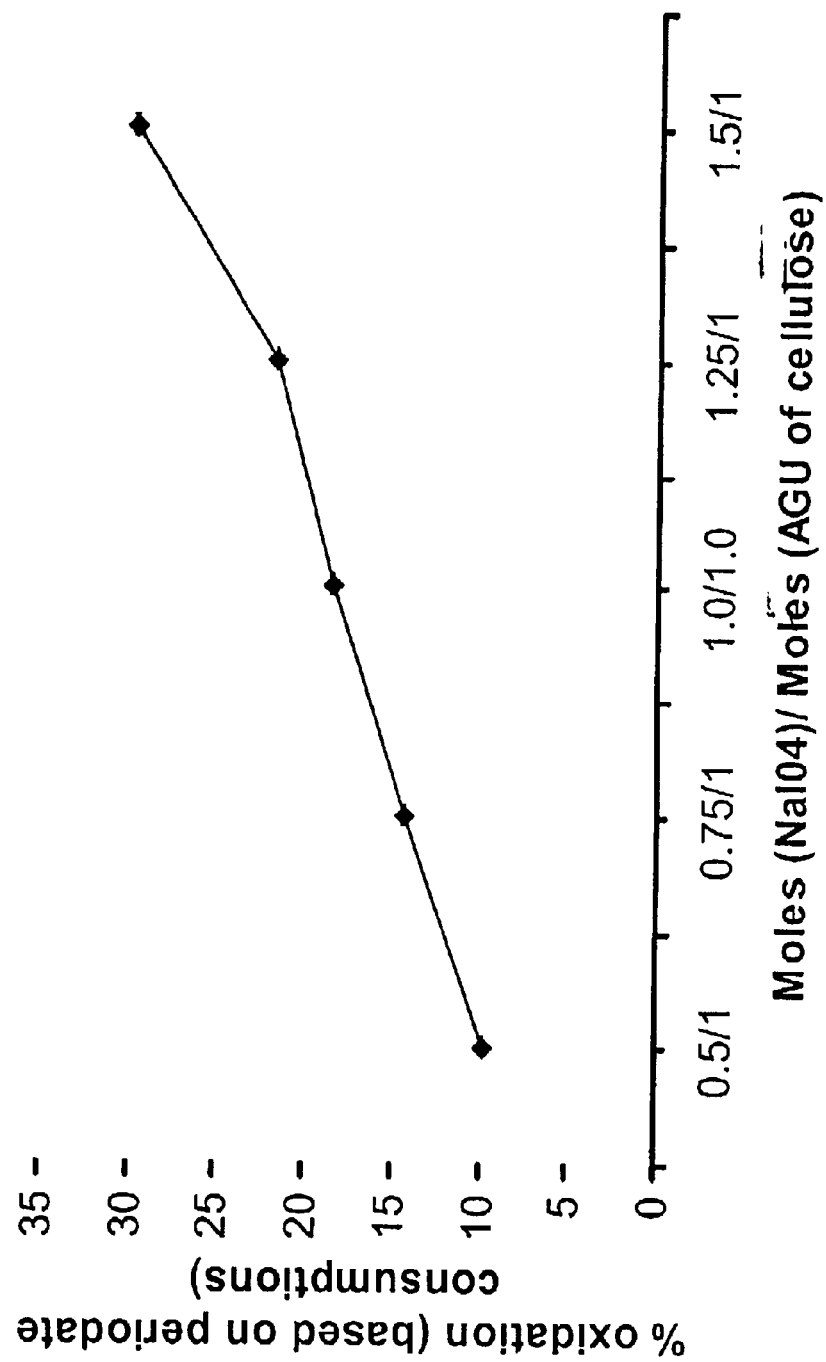
FIG. 2 is a graph illustrating the effect of periodate concentration on oxidation, as described in Example 2. The reaction duration is 3 hours at ambient temperature.

The relationship between oxidation level and the concentration of periodate used in the reaction is shown in FIG. 2.

X-Ray Diffraction

Figure 3:
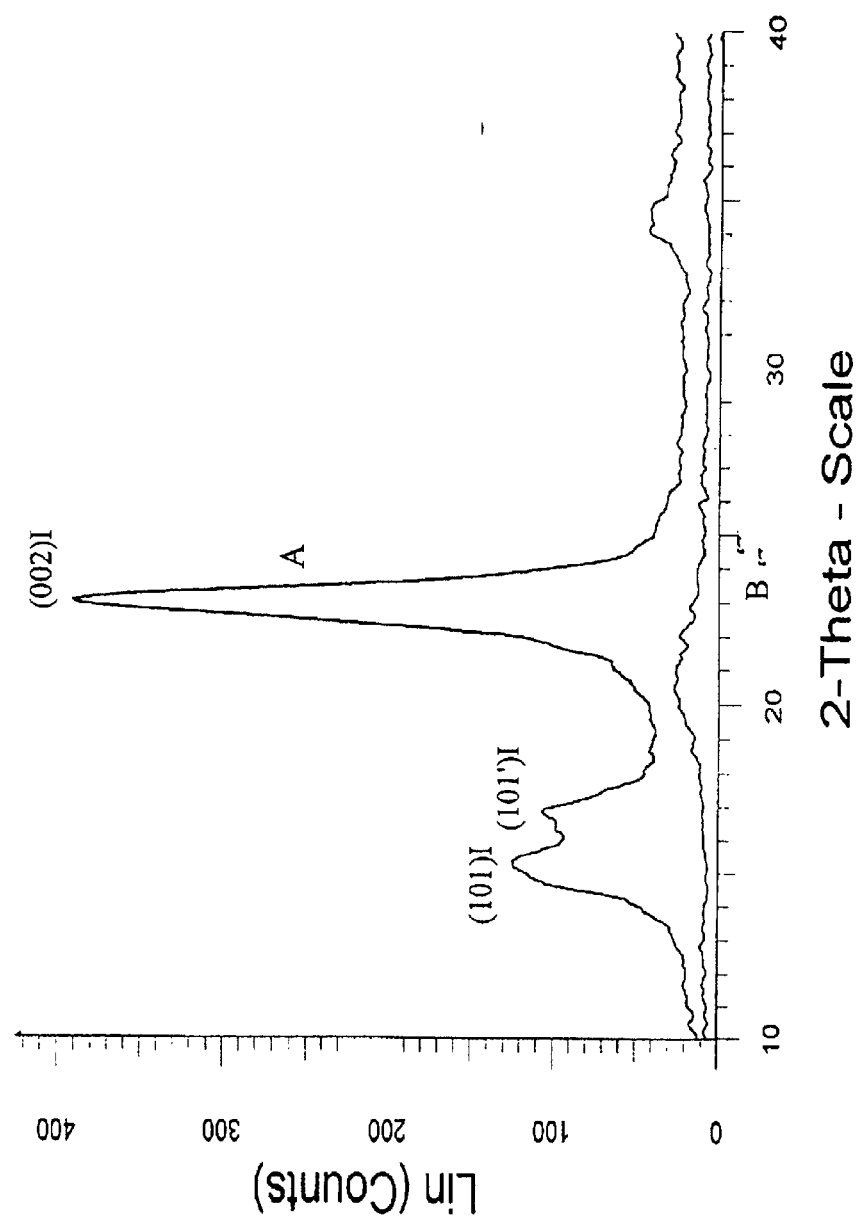
FIG. 3 is a graph illustrating the X-ray diffractograms of A) cotton linter; and B) regenerated cellulose, as described in Example 2.

The X-ray diffraction measurements on dried membranes over a 10–40° 2θ range on a Siemens Model D5000 diffractometer, equipped with monochromatic CuKα ($\alpha_1$=1.54060 Å, ($\alpha_2$=1.54438 Å) X-rays. The diffractograms are set forth in FIG. 3.

Microscopic Study

Three samples from each of the film specimens (thickness: 0.40 mm) was used to measure the pore size and morphology of films on SEM photographs. The native, uncoated specimens (in hydrated form) were studied under Hitachi scanning electron microscope (Hitachi=S2460N, Hitachi Ltd, Tokyo, Japan) operating at 20 kv. Secondary electron images were taken. Image analysis of SEM photographs were performed by using the public domain NIH Image program (http://rsb.info.nih.gov/nih-image/).

Fourier-Transform Infrared Spectroscopy

Figure 4:
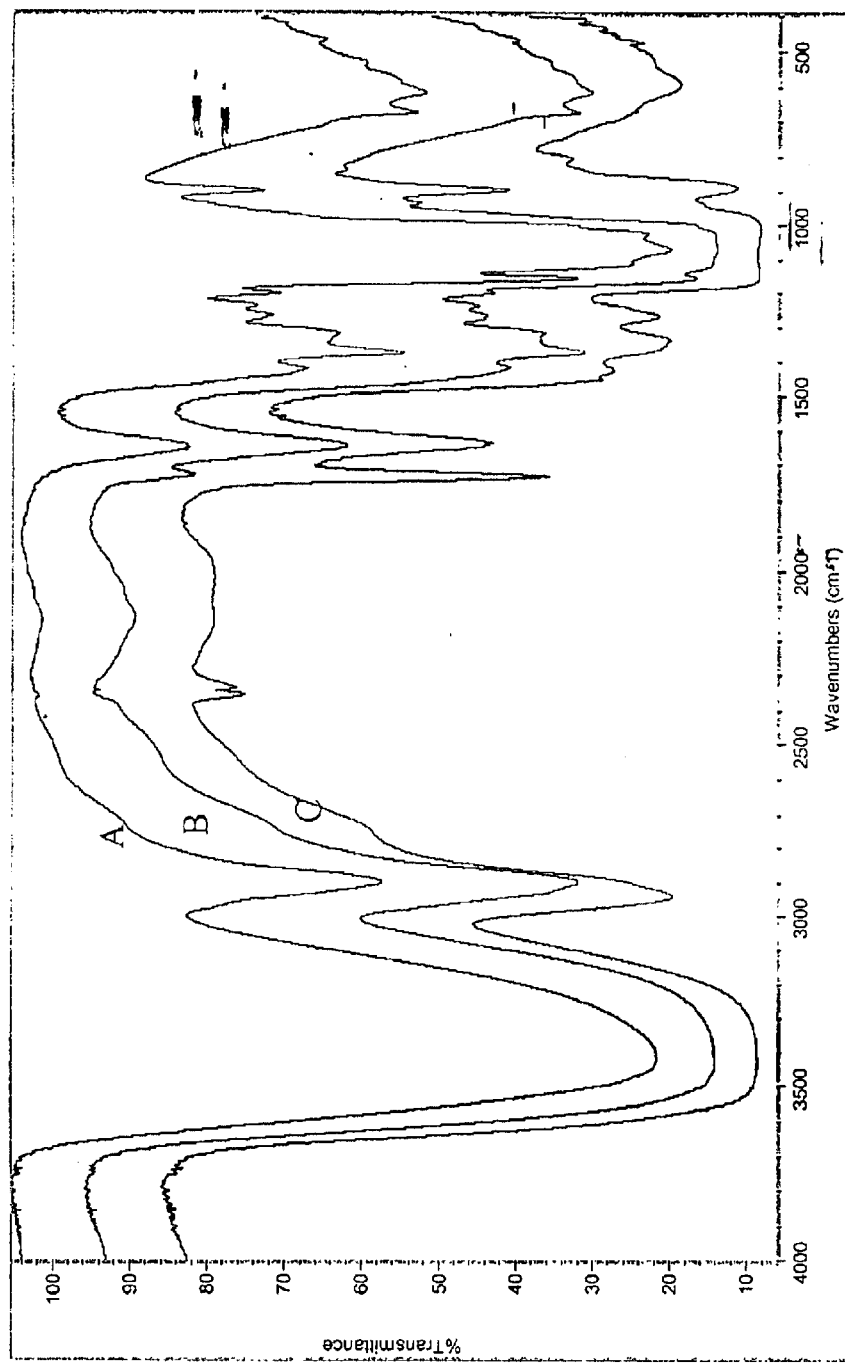
FIG. 4 is a graph illustrating the infrared spectra of A) regenerated cellulose film; B) 23% oxidized regenerated cellulose film; and C) 71% oxidized regenerated cellulose film, as described in Example 2.

Membranes dried at 105° C. for 2 hours were used to obtain Fourier transform infrared (FTIR) spectra. The infrared spectra were recorded by Nicolet Magna 860. The results are shown in FIG. 4.

Results

Regeneration of cellulose in water resulted in hydrated, transparent and flexible regenerated cellulose membranes.

The diffractogram of cotton linter contains well-defined peaks due to reflectances of the 002, 101 and 101' planes of the cellulose I crystalline lattice, indicating a relatively high degree of cellulose I crystallinity. In contrast, the regenerated cellulose exhibits a diffuse halo characteristic of amorphorous cellulose.

The porosity and pore morphology are obviously dependent on the amount of salt and particle size of salt. Porosity increases with increasing amount of salt. High salt loading resulted in highly interconnected pore structure, which is not observed in low salt loading. With increasing particle size of NaCl, an increase in pore size is observed. The crossection of a porous RC membrane prepared using 60% w/w of NaCl showed a relatively open, well-connected network structure. It was observed that as particle size range increased there was an increase in irregularity of pore sizes and shapes. Pore shapes are mostly circular and elliptical. For the largest size range, the pore size on the surface varied from very small to very large interconnecting pores.

Periodate oxidation is characterized by the selective, oxidative cleavage of the $C_2$–$C_3$ bond of the glucopyranose ring. The reaction is accompanied by the formation of reactive dialdehyde units at the $C_2$ and $C_3$ sites. At physiological pH, 2,3-dialdehyde cellulose degrades into glycolic acid and 2,4-dihydroxy butyric acid.

FIG. 2 shows the increase in oxidation levels with increased mole to mole ratio of $NaIO_4$ to anhydroglucose unit of cellulose, determined by periodate consumption. FIG. 1 indicates that the higher temperature (45° C.) favored higher oxidation levels.

The molecular structure was confirmed by IR spectroscopy. In FIG. 4, a distinct new peak appeared in the region 1732 cm$^{-1}$, for the periodate oxidized samples, but no such peak was observed for the non-oxidized cellulose samples. This peak can be attributed to the C=O stretching vibration in the free aldehyde.

Conclusions

It is possible to tailor the degree of oxidation and morphology of the materials by simply varying the processing parameters, like temperature and quantity of salt. The porosity and pore size can be controlled by varying the amount and particle size of the salt.

The mechanical and degradation properties of these materials exhibit a goods compromise of mechanical and degradation properties. The aldehyde functional group provides a site for attachment of drugs, proteins, and cells.

From the above it can be seen that the invention accomplishes all of its stated objectives.

What is claimed is:

1. A scaffold comprising: oxidized regenerated cellulose, said cellulose being 2-functionalized, 3-functionalized, or 2,3-functionalized, said cellulose not being functionalized at the 6-position.

2. The scaffold of claim 1 that is derived from a natural, non-microbial source.

3. The scaffold of claim 1 having interconnecting pores.

4. The scaffold of claim 3 wherein the pores are highly interconnected.

5. The scaffold of claim 3 wherein the pores have an average diameter of between about 80–90 μm.

6. The scaffold of claim 1 that is in a form selected from the group consisting of a sheet, hollow tube, and a film.

7. The scaffold of claim 1 further including at least one substance attached to the molecule or molecules, whereby the substance is selected from the group consisting of a cell, a drug, a protein, and a peptide.

8. A composition for the treatment of tissue damage, which comprises the scaffold of claim 1; and human or animal cells.

9. A method of treating tissue damage comprising: applying the composition of claim 1 to an area of tissue damage in an animal or human; and allowing the animal or human cells to adhere or adsorb to the scaffold.

10. An artificial blood vessel comprising the scaffold of claim 1.

11. The scaffold of claim 1 that is functionalized with one or more molecules selected from the group consisting of: carboxyl, aldehyde, and ketone.

12. The scaffold of claim 1 that is flexible.

13. A method of making a scaffold comprising: dissolving cellulose in a solvent or solvent system to create a cellulose mixture, whereby the solvent or solvent system further includes a porogen that is insoluble in DMSO; casting or molding the cellulose mixture into a desired shape; and regenerating the cellulose in water to form a scaffold.

14. The method of claim 13 whereby the cellulose mixture is cast or molded by spreading the solution on an apparatus selected from the group consisting of a petri dish, glass plate, and hollow tube.

15. The method of claim 14 whereby the scaffold is oxidized to produce carboxyl groups, and further including the step of adding to amine functional groups on the scaffold.

16. The method of claim 14 whereby the scaffold is oxidized to produce aldehyde groups, and further including the step of adding amine functional groups on the scaffold.

17. The method of claim 13 further including the step of oxidizing the scaffold by placing the scaffold in an oxidant to produce one or more functional groups selected from the group consisting of carboxyl, aldehyde, and/or ketone functional groups on the scaffold.

18. The method of claim 17 wherein the oxidant is selected from the group consisting of gaseous chlorine, hydrogen peroxide; peracetic acid, chlorine dioxide, persulfates, hypochlorous acid, hypohalites, and periodates.

19. The method of claim 13 whereby the cellulosic source is selected from the group consisting of cotton, paper, cotton linters, α-cellulose, wood pulp, purified wood pulp, microcrystalline cellulose, powdered cellulose, low crystallinity cellulose, and microfibrillated cellulose.

20. The method of claim 13 whereby the solvent system is DMSO and paraformaldehyde.

21. A method of making a scaffold comprising: dissolving cellulose in a solvent or solvent system to crease a cellulose mix fire, whereby the solvent or solvent system further includes a porogen, said porogen being selected from the group consisting of sucrose, lactose, galactose, fructose, sodium chloride, and potassium chloride; casting or molding the cellulose mixture into a desired shape; and regenerating the cellulose in water to form a scaffold.

22. A scaffold comprising: oxidized regenerated cellulose, whereby the cellulose is functionalized with one or more molecules selected from the group consisting of: carboxyl, aldehyde, ketone, and hydroxyl, said cellulose being flexible, said cellulose not being 6-functionalized.

23. A method of making a scaffold comprising dissolving cellulose in a solvent or solvent system to create a cellulose mixture, whereby the solvent or solvent system further includes a porogen, said porogen being selected from the group consisting of sucrose, lactose, galactose, fructose, sodium chloride, and potassium chloride; casting or molding the cellulose mixture into a desired shape; and regenerating the cellulose in water to form a scaffold.

24. The method of claim 23 wherein the porogen is sodium chloride.

* * * * *

UNITED STATES PATENT AND TRADEMARK OFFICE
CERTIFICATE OF CORRECTION

PATENT NO.   : 6,800,753 B2
DATED        : October 5, 2004
INVENTOR(S)  : Kumar, Vijay It is certified that error appears in the above-identified patent and that said Letters Patent is hereby corrected as shown below:

Title page,
Item [54], Title, should read -- REGENERATED CELLULOSE AND OXIDIZED REGENERATED CELLULOSE MEMBRANES AS POTENTIAL BIODEGRADABLE SCAFFOLDS FOR DRUG DELIVERY AND TISSUE ENGINEERING --

Column 11,
Lines 13-14, should read -- cellulose in a solvent or solvent system to create a cellulose mixture, whereby the solvent or solvent system further --

Signed and Sealed this

Twenty-first Day of December, 2004

JON W. DUDAS
*Director of the United States Patent and Trademark Office*